United States Patent
Kang et al.

(10) Patent No.: US 10,878,216 B2
(45) Date of Patent: Dec. 29, 2020

(54) APPARATUS AND METHOD FOR MEASURING SIGNAL AND OBTAINING BIO-INFORMATION

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/268,028

(22) Filed: Feb. 5, 2019

(65) Prior Publication Data

US 2020/0019745 A1    Jan. 16, 2020

(30) Foreign Application Priority Data

Jul. 12, 2018    (KR) .................. 10-2018-0081264

(51) Int. Cl.
*G06K 9/00*    (2006.01)
*G06K 9/46*    (2006.01)

(52) U.S. Cl.
CPC ....... *G06K 9/0004* (2013.01); *G06K 9/00885* (2013.01); *G06K 9/00912* (2013.01); *G06K 9/4647* (2013.01); *G06K 2009/00939* (2013.01)

(58) Field of Classification Search
CPC ............ G06K 9/0004; G06K 9/00885; G06K 9/00912; G06K 9/4647; G06K 2009/00939
See application file for complete search history.

(56) References Cited

U.S. PATENT DOCUMENTS

| 7,818,052 | B2 | 10/2010 | Litvak et al. | |
|---|---|---|---|---|
| 9,349,035 | B1 | 5/2016 | Gerber et al. | |
| 9,867,513 | B1* | 1/2018 | Hall | A47K 13/24 |
| 2005/0207627 | A1* | 9/2005 | Lee | G06K 9/00067 382/124 |
| 2014/0368715 | A1* | 12/2014 | Shih | G01N 21/41 348/311 |
| 2015/0193669 | A1 | 7/2015 | Gu et al. | |
| 2016/0210513 | A1* | 7/2016 | Wang | G06K 9/629 |
| 2016/0239701 | A1* | 8/2016 | Lee | G06K 9/00026 |

(Continued)

FOREIGN PATENT DOCUMENTS

JP       10-255050 A     9/1998
KR    10-2006-0081178 A   7/2006

(Continued)

OTHER PUBLICATIONS

Communication dated Aug. 6, 2019, issued by the European Patent Office in counterpart European Application No. 19161832.1.

(Continued)

*Primary Examiner* — Stephen G Sherman
(74) *Attorney, Agent, or Firm* — Sughrue Mion, PLLC

(57) ABSTRACT

An apparatus for measuring a signal is provided. The apparatus for measuring a signal may include a sensor configured to generate pixel data representing a fingerprint image of an object by detecting light scattered or reflected from the object and a processor configured to acquire the fingerprint image of the object based on the pixel data and acquire a pulse wave signal based on the fingerprint image and the pixel data.

12 Claims, 21 Drawing Sheets

(56) References Cited

U.S. PATENT DOCUMENTS

| | | | |
|---|---|---|---|
| 2017/0071516 A1 | 3/2017 | Bhagat et al. | |
| 2017/0119262 A1 | 5/2017 | Shim et al. | |
| 2017/0286748 A1 | 10/2017 | Kim et al. | |
| 2017/0316419 A1 | 11/2017 | Laporta | |
| 2017/0337412 A1* | 11/2017 | Bhat | G06K 9/0004 |
| 2018/0096119 A1 | 4/2018 | Yun et al. | |

FOREIGN PATENT DOCUMENTS

| | | |
|---|---|---|
| KR | 10-2017-0032877 A | 3/2017 |
| KR | 10-2017-0043294 A | 4/2017 |
| KR | 10-2017-0111814 A | 10/2017 |
| KR | 10-2018-0017523 A | 2/2018 |
| WO | 2016/159523 A1 | 10/2016 |

OTHER PUBLICATIONS

Lai-Man Po, et al., "Frame Adaptive ROI for Photoplethysmography Signal Extraction from Fingertrip Video Captured by Smartphone", May 24, 2015, IEEE International Symposium on Circuits and Systems, XP033183495, p. 1634-1637, 4 pages total.

* cited by examiner

FIG. 3B

APPARATUS AND METHOD FOR MEASURING SIGNAL AND OBTAINING BIO-INFORMATION

CROSS-REFERENCE TO RELATED APPLICATION(S)

This application claims priority from Korean Patent Application No. 10-2018-0081264, filed on Jul. 12, 2018 in the Korean Intellectual Property Office, the disclosure of which is incorporated herein by reference in its entirety.

BACKGROUND

1. Field

Apparatuses and methods consistent with exemplary embodiments relate to measuring a signal from an object and obtaining bio-information by using an image sensor.

2. Description of Related Art

Generally, as examples of methods of non-invasively measuring blood pressure without causing pain or discomfort to the human body, there are a method of measuring blood pressure through cuff-based pressure measurement and a method of estimating blood pressure through pulse wave measurement without a cuff.

The cuff-based blood pressure measurement method may include a Korotkoff-sound method and an oscillometric method. In the Korotkoff-sound method, a cuff is wrapped around an upper arm, a pressure inside the cuff is increased, and blood pressure is measured by listening to sound produced in a blood vessel by a stethoscope along with the reduction of the pressure in the cuff. In the oscillometric method, which uses an automated machine, a cuff pressure is increased after a cuff is wrapped around an upper arm, a pressure inside the cuff is continuously monitored by gradually reducing the cuff pressure, and then blood pressure is measured based on a point where a large change in pressure signal occurs.

As cuff-less blood pressure measurement methods, there are generally a method of estimating blood pressure by calculating a pulse transit time (PTT) and a pulse wave analysis (PWA) method of estimating blood pressure by analyzing a pulse waveform.

SUMMARY

According to an aspect of an exemplary embodiment, there is provided an apparatus for measuring a signal, including: a sensor configured to generate pixel data representing a fingerprint image of an object by detecting light scattered or reflected from the object; and a processor configured to acquire the fingerprint image of the object based on the pixel data and acquire a pulse wave signal based on the fingerprint image and the pixel data.

The processor may be further configured to set a region of interest (ROI) on the fingerprint image and acquire the pulse wave signal based on intensities of pixels in the ROI among the pixel data.

The pulse wave signal may include a photoplethysmography (PPG) signal.

The processor may be further configured to estimate an amplitude value of the PPG signal based on the intensities of the pixels in the ROI.

The processor may be further configured to estimate the amplitude value of the PPG signal by calculating at least one of an average, a median value, a lowest value, and a highest value of the intensities of the pixels.

The processor may be further configured to extract a feature point from the fingerprint image and set the ROI based on at least one of a position and an orientation of the feature point.

The feature point may include a fingerprint core point.

The processor may be further configured to generate information to guide a user to change of a position of the object in response to the position of the feature point being outside a predetermined normal range on the fingerprint image.

The apparatus may further include one or more light emitting didoes (LEDs) or one or more laser didoes as a light source configured to emit the light to the object.

The apparatus may further include a display panel as a light source configured to emit the light to the object.

The apparatus may further include a light source configured to emit the light to the object in a predetermined light emission pattern under the control of the processor, and the light emission pattern may include at least one of an emission color and an emission shape including at least one of a straight line shape, a concentric circle shape, a rectangular shape, and a diagonal shape.

The sensor may include a pixel array configured to detect the light scattered or reflected from the object and each pixel may include at least one of a photodiode and a photo transistor.

According to an aspect of another exemplary embodiment, there is provided a method of measuring a signal, including: generating pixel data representing a fingerprint image of an object by detecting light scattered or reflected from the object; acquiring a fingerprint image of the object based on the pixel data; and acquiring a pulse wave signal based on the acquired fingerprint image and the pixel data.

The acquiring the pulse wave signal may include setting a region of interest (ROI) on the fingerprint image and acquiring the pulse wave signal based on intensities of pixels in the ROI among the pixel data.

The acquiring the pulse wave signal may further include extracting a feature point from the fingerprint image and the setting of the ROI comprises setting the ROI based on at least one of a position and an orientation of the feature point.

The feature point may include a fingerprint core point.

The acquiring the pulse wave signal may include determining whether the position of the feature point is outside a predetermined normal range on the fingerprint image and generating information to guide a user to change of a position of the object in response to determining that the position of the feature point is outside the predetermined normal range.

According to an aspect of another exemplary embodiment, there is provided an apparatus for measuring a signal, including: a first sensor configured to generate pixel data representing a fingerprint image of an object; a second sensor arranged around the first sensor and configured to measure a pulse wave signal by detecting light scattered or reflected from the object; and a processor configured to acquire a fingerprint image of the object based on the pixel data and control driving of the second sensor based on the fingerprint image.

The first sensor may include a capacitance-based image sensor or a fingerprint sensor.

The second sensor may include a plurality of channels arranged in a circle and a rectangle around the first sensor.

Each of the plurality of channels may include one or more light sources configured to emit the light to the object to be scatted or reflected therefrom, and one or more detector configured to detect the light scattered or reflected from the object.

The processor may be further configured to extract a feature point from the fingerprint image and control driving of the plurality of channels based on at least one of a position and an orientation of the feature point.

The processor may be further configured to drive a first channel arranged in a direction of the feature point and a second channel arranged in a direction opposite to the direction of the feature point among the plurality of channels.

The processor may be further configured to drive a light source of the first channel and a detector of the second channel, and the light source and the detector may be disposed apart from the feature point by a predetermined distance.

The processor may be further configured to alternately drive a pair of a light source of the first channel and a detector of the second channel and a pair of a detector of the first channel and a light source of the second channel in a time division manner for a predetermined time period. The first channel and the second channel may be disposed apart from the feature point by a predetermined distance.

The processor may be further configured to generate information to guide a user to change the position of the object in response to the position of the feature point being outside a predetermined normal range on the fingerprint image.

The processor may be further configured to obtain bio-information based on the pulse wave signal, and the bio-information may include at lease one of blood pressure, vascular age, a degree of arteriosclerosis, aortic pressure waveform, vascular compliance, stress index, and a degree of fatigue.

BRIEF DESCRIPTION OF THE DRAWINGS

The above and/or other aspects will be more apparent by describing certain exemplary embodiments, with reference to the accompanying drawings, in which:

FIGS. 3A, 3B, and 3C are diagrams for describing a method of acquiring a target signal;

DETAILED DESCRIPTION

Figure 1A:
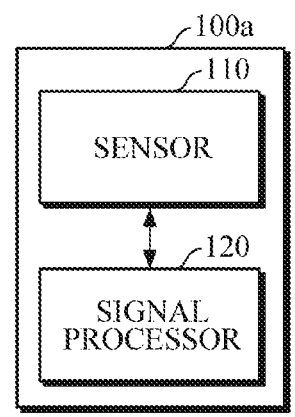
FIGS. 1A, 1B, and 1C are block diagrams illustrating an apparatus for measuring a signal according to exemplary embodiments.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms "first," "second," etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising" will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Various exemplary embodiments of an apparatus for measuring a signal described hereinafter may be mounted in a variety of information processing devices, such as a portable wearable device, a smart device, and the like. For example, the various information processing devices may include wearable devices of various types, such as a smartwatch worn on a wrist, a smart band type, a headphone type, a hairband type, and the like, and mobile devices, such as a smartphone a tablet personal computer (PC), and the like. However, the information processing devices are not limited to the aforementioned examples.

Figure 1B:
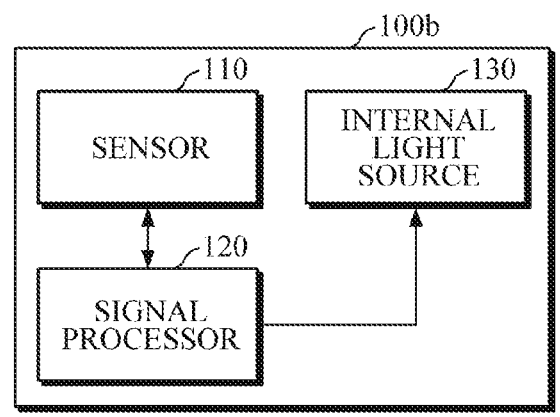
Figure 1C:
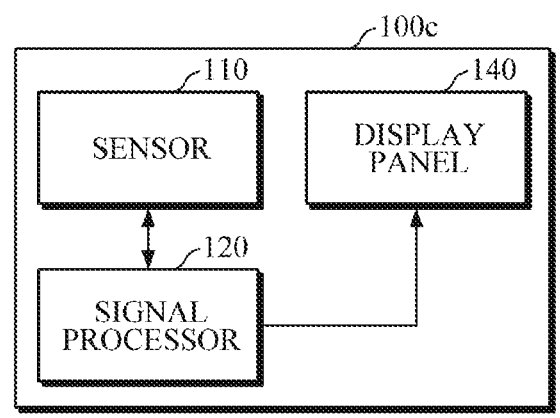

FIGS. 1A to 1C are block diagrams illustrating an apparatus for measuring a signal according to exemplary embodiments. FIGS. 2A to 2D are diagrams for describing a sensor of the apparatus of FIGS. 1A to 1C.

Referring to FIG. 1A, the apparatus 100a for measuring a signal includes a sensor 110 and a signal processor 120.

The sensor 110 may detect light scattered or reflected from an object and generate pixel data representing a contact image of the object. The sensor 110 may generate consecutive pixel data during the contact with the object. A light source may be disposed outside the apparatus 100a, and may emit a light to the object so that the light is reflected or scattered from the object and collected by the sensor 110. The sensor 110 may detect the light reflected or scattered according to a tissue component of the object.

The sensor 110 may include, but not limited to, an optical-based image sensor, such as a complementary metal-oxide-semiconductor (CMOS) image sensor (CIS), or a fingerprint sensor. The sensor 110 may include a pixel array, and each pixel of the pixel array may include a detector, such as a photodiode or a photo transistor, for detecting light and converting the light into an electrical signal. For example, the sensor 110 may convert an optical signal detected by each pixel into an electrical signal, for example, an electric charge signal or a voltage signal, so as to output an electric signal of each pixel as pixel data.

The signal processor 120 may be electrically connected to the sensor 110 and may obtain a contact image of the object based on the pixel data received from the sensor 110. The signal processor 120 may obtain successive contact images using consecutive pixel data continuously received. In particular, the object may be a finger and the obtained contact image may be a fingerprint image of the finger.

In addition, the signal processor 120 may acquire a target signal necessary for analysis of the object based on the acquired contact images and pixel data. In particular, the target signal may include a biosignal, a bioelectrical signal, a pulse wave signal. The pulse wave signal may include an electrocardiography (ECG) signal and a photoplethysmography (PPG) signal, but is not limited thereto.

For example, when the signal processor 120 acquires the contact image using the pixel data, the signal processor 120 may extract a feature point from the acquired contact image. When the contact image is a fingerprint image, the feature point may be a fingerprint core point, but is not limited thereto, such that it may be appropriately defined by taking into account characteristics of the user's fingerprint, for example, a thickness or wound on a finger region. A direction of the feature point may be determined based on a center point of the contact image. Alternatively, when the contact image is a fingerprint image, the direction of the feature point may be a direction of a fingerprint.

The signal processor 120 may set a region of interest (ROI) on the contact image based on the extracted feature point. The signal processor 120 may set the ROI based on a position and/or direction of the feature point. In particular, the ROI may be set to various shapes, such as a circle, a triangle, a rectangle, and a free curve, and the like, and/or various sizes, in advance. For example, in the case in which the user repeatedly lift and rest his/her finger on the sensor 110, the contact position of the finger may be changed. In particular, the position and/or direction of the extracted feature point is changed, and hence the signal processor 120 may set a position, shape, or size of the ROI differently according to the position and/or direction of the feature point.

Once the ROI is set, the signal processor 120 may acquire a target signal based on an intensity of each pixel belonging to the ROI among the pixel data. In particular, an electrical signal intensity of each pixel, or a value converted from an electrical signal through preprocessing, such as normalization, may be defined as the intensity of each pixel. The intensity of each pixel may vary according to a contact time or contact area between the object and the sensor 110. For example, when the user's finger in contact with the sensor 110 is pressed against the sensor 110 with an gradually increasing force, the contact time and contact area are gradually increased and in turn the intensity of an electrical signal of each pixel may also be increased.

The signal processor 120 may acquire a pulse wave signal as a target signal based on such characteristics. For example, the signal processor 120 may use an ROI of a contact image acquired at a specific point in time to estimate an amplitude value at the specific point in time. At this time, pixel intensities inside the ROI may be input to an amplitude estimation equation and a value calculated by the amplitude estimation equation may be estimated as the amplitude value at the specific point in time. The amplitude estimation equation may be an equation to calculate one of an average value, a median value, the lowest value, and the highest value of pixel intensities as an amplitude value. However, the amplitude estimation equation is not limited thereto, and may be defined as various liner or nonlinear function forms.

When the feature point is extracted from the contact image, the signal processor 120 may determine whether the extracted feature point falls outside a normal range, and may guide the user to change a contact position of the object when the extracted feature point is outside the normal range. For example, when the feature point is completely outside a detection region of the sensor 110, in other words, when the feature point does not fall within the contact image, it may be determined that the feature point falls outside the normal range. In particular, the normal range may be set based on a center of the contact image (e.g., a center of the detection region of the sensor 110). For example, the normal range may correspond to an area within a predetermined distance from the center of the contact image or the center of the detection region of the sensor 110. Alternatively, it is possible to set an appropriate user-specific detection region of the sensor 110 according to characteristics of an object of each user, for example, characteristics of a fingerprint, or the like.

Meanwhile, a method of guiding the user to change the contact position is not necessarily limited to a specific method. For example, guide information may be output through an output module mounted in the apparatus and/or an output module mounted in an external device connected to the apparatus. In particular, the output module may include a voice output module, such as a speaker, a visual output module, such as a display, or a haptic module capable of transmitting vibration or tactile sensation to the user, but the output module is not limited thereto.

Referring to FIG. 1B, in addition to a sensor 110 and a signal processor 120, the apparatus 100b may further include an internal light source 130 configured to emit light to an object under the control of a signal processor 120.

The internal light source may include a light emitting diode (LED) or a laser diode, and may be formed as one or a plurality of arrays. The internal light source 130 may emit light to the object under the control of the signal processor 120. The internal light source 120 may be configured to emit light rays of different wavelengths.

When the internal light source 130 is formed as a plurality of arrays, the signal processor 120 may control the internal light source 130 to emit light according to a predetermined light emission pattern. For example, the light emission pattern may be defined in advance as various combinations of emission shapes of the entire arrays of the light sources 130 and/or emission color of each light source. In particular, the emission shape may include a straight line shape, a concentric circle shape, a rectangular shape, a diagonal shape, and the like, but is not limited thereto. In addition, the light emission pattern may be defined to be differed according to various measurement situations, such as a measurement time and/or an object to be measured.

In particular, the sensor 110 may detect light reflected or scattered from the object which is irradiated by the internal light source 130, and may generate pixel data based on the detected light.

The signal processor 120 may acquire a contact image by receiving the pixel data from the sensor 110 and acquire a desired target signal based on the acquired contact image and pixel data.

Referring to FIG. 1C, the apparatus 100c for measuring a signal may further include a display panel 140, in addition to a sensor 110 and a signal processor 120. In addition, the apparatuses 100b and 100c for measuring a signal shown in FIGS. 1B and 1C may be integrated into one apparatus as needed. For example, one apparatus for measuring a signal may be configured to include both the internal light source 130 and the display panel 140.

According to the present embodiment, part of light emitted from the display panel 140 may be used as a light source for acquiring the contact image. The display panel 140 may include pixels that generate light to irradiate the object. The display panel 140 may display the contact image acquired by the signal processor 120. Here, the display panel 140 may be implemented using generally known techniques, and thus a detailed description thereof will be omitted.

The signal processor 120 may be connected to the display panel 140 and control the pixels of the display panel 140 to emit light in a predetermined light emission pattern. The predetermined light emission pattern is as described above.

Figure 2A:
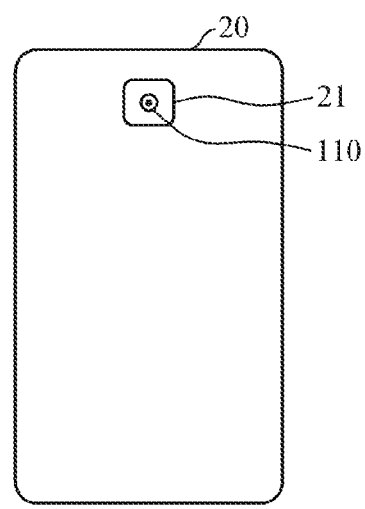
FIGS. 2A, 2B, 2C, and 2D are diagrams for describing a sensor of the apparatus of FIGS. 1A to 1C.
Figure 2B:
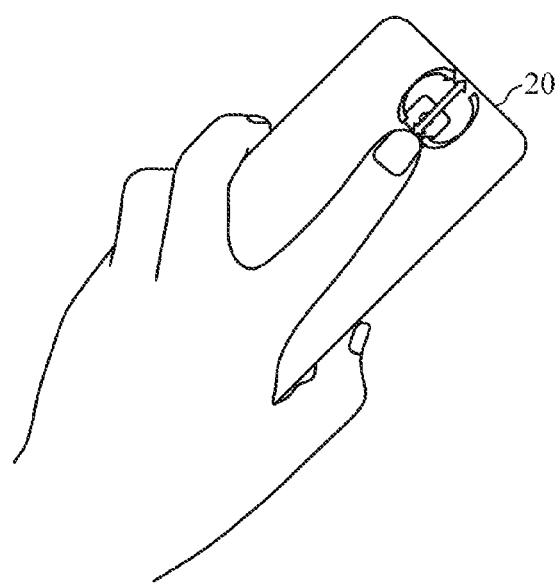
Figure 2C:
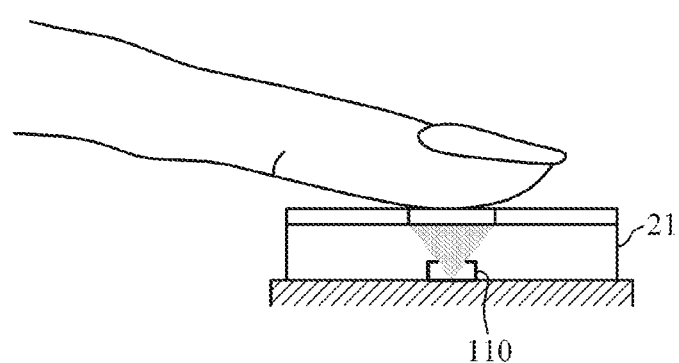

FIGS. 2A to 2D illustrate examples in which the apparatus 100a, 100b, and 100c is mounted in a smart device 20. According to one exemplary embodiment, as shown in FIGS. 2A to 2C, a sensor 110 may be mounted in a rear sensor unit 21 of the smart device 20. A filter array including color filters for transmitting or blocking light of a predetermined wavelength region to each pixel of the sensor 110 may be arranged in the rear sensor unit 21. In addition, a micro-lens may be arranged on each pixel of the sensor 110 in order to increase, for example, light gathering power of each pixel. In particular, light emitted from a surrounding environment of the smart device 20 may be used as an external light source. Alternatively, the internal light source 130 may be mounted at a predetermined position on a rear surface of the smart device 20, for example, around or inside the rear sensor unit 21.

Figure 2D:
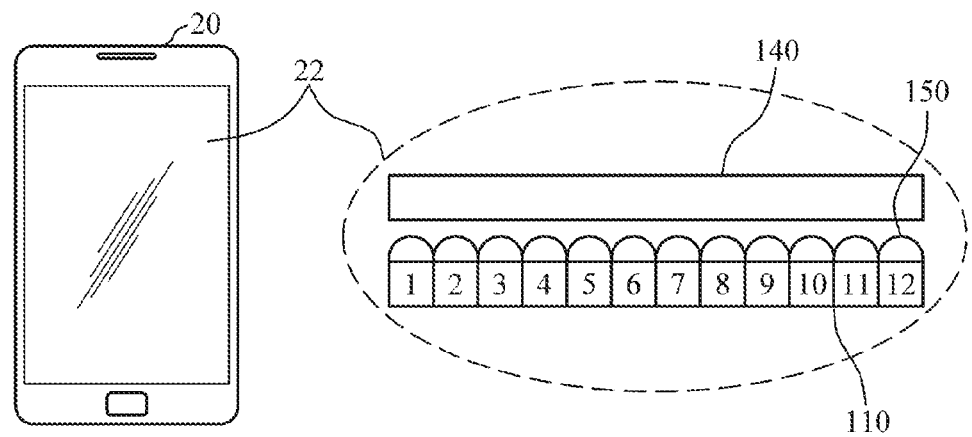

In another example, as shown in FIG. 2D, the sensor 110 may be mounted on a front sensor unit 22 of the smart device 20. The front sensor unit 22 may include the display panel 140 and the display panel 140 may include a touch sensor configured to process a user's touch input and a touch screen configured to display a variety of information. In addition, a filter array including color filters for transmitting or blocking light of a predetermined wavelength region to each pixel of the sensor 110 may be arranged in the front sensor unit 22. Also, a micro-lens 150 may be arranged on each pixel of the sensor 110 in order to increase light gathering power as sown in FIG. 2D. In particular, light emitted from a surrounding environment may be used as an external light source, or the internal light source 130 may be mounted on a front surface, for example, an upper part of the front surface, of the smart device 20. Additionally, light emitted from the display panel 140 may be used as a light source to be input to the object. When the light emitted from the display panel 140 is input to the object and then light is reflected or scattered from the object, the scattered or reflected light may be detected by the sensor 110, passing through fine holes formed on the display panel 140.

According to the present embodiment, as shown in FIG. 2B, even when the contact position of the finger is frequently changed or when the center of a fingerprint is different from the center of an area, it is possible to acquire an accurate target signal.

Figure 3A:
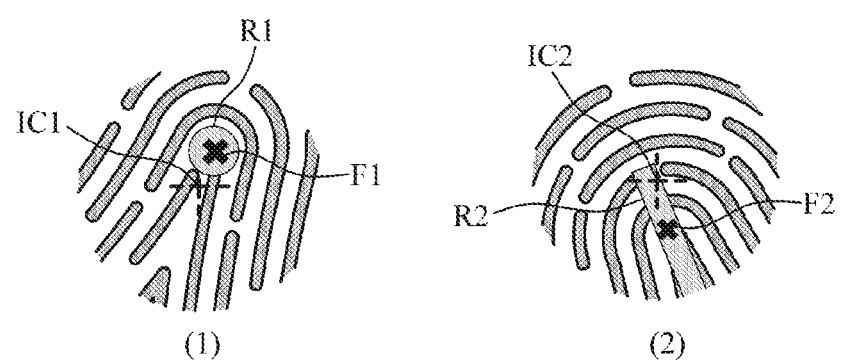
Figure 3B:
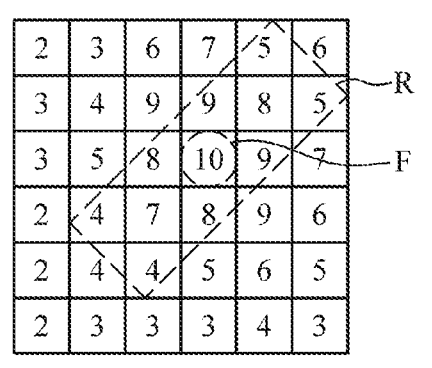
Figure 3C:
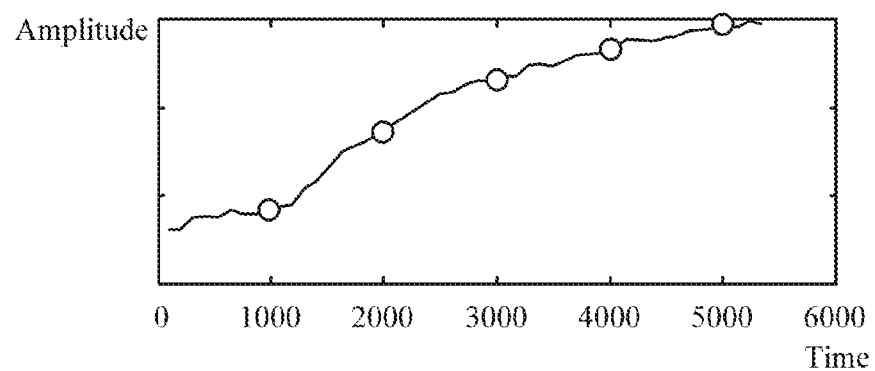

FIGS. 3A to 3C are diagrams for describing a method of the signal processors 120 of FIGS. 1A to 1C to acquire a target signal.

FIG. 3A illustrates a contact image, that is, a fingerprint image of a finger, acquired by the signal processor 120 based on pixel data. When the fingerprint image is acquired, the signal processor 120 may extract a feature point, for example, a fingerprint core point F1 or F2, from the fingerprint image and set an ROI R1 or R2 based on the extracted fingerprint core point F1 or F2. The size of the ROI R1 or R2 may be defined in advance. As illustrated in FIG. 3A, a center of the ROI R1 or R2 may be set to be located at the position of the feature point F1 or F2, but is not limited thereto. For example, when the fingerprint core point is located at either side of the fingerprint image, the ROI may be set to be shifted toward the center of the fingerprint image with respect to the fingerprint core point.

FIG. 3A illustrates an image (1) in which the extracted fingerprint core point F1 is located on the right side slightly above the center IC1 of the fingerprint image and the ROI R1 is set as a circle with respect to the fingerprint core point F1. For example, the ROI R1 may be set to a circle having the fingerprint core point F1 as the center of the circle, with a predetermined radius. FIG. 3A illustrates an image (2) in which the fingerprint core point F2 is located on the lower right side from the center IC2 of the fingerprint image and the ROI R2 is set as a rectangle with respect to the fingerprint core point F2. In particular, the rectangular ROI may be set in consideration of the orientation of the fingerprint. For example, a long side of the rectangle may be set to be parallel to a line connecting the center IC2 of the fingerprint image and the fingerprint core point F2.

FIG. 3B illustrates an example of pixel data acquired by the sensor 110 at a specific point in time, showing a feature point F and an ROI R on the pixel data. A value in each pixel of FIG. 3B represents a pixel intensity. When the extraction of the feature point F and setting of the ROI R are completed, the signal processor 120 may estimate an amplitude value at a specific point in time by inputting intensities of pixels belonging to the ROI R to an amplitude estimation equation below. The amplitude estimation equation of Equation 1 is an example of an average calculation formula, and an amplitude value at a specific point in time may be estimated as 7, which is an average of the pixel intensities of the ROI R of FIG. 3B, by using Equation 1.

$$\text{Amp} = \frac{P_1 + \ldots + P_N}{N} \quad (1)$$

Here, Amp represents an estimated amplitude value and $P_1$ to $P_S$ each represent an intensity of each of N pixels in an ROI.

FIG. 3C illustrates a pulse wave signal acquired using pixel data continuously measured for a predetermined period of time. Here, an X-axis represents a time index for a measurement time and a Y-axis represents an amplitude value at each point in time. When the user increases a contact time and a contact pressure by increasing a pressing force of a finger pressing the sensor 110, the pixel intensity of the pixel data shows a tendency to also increase in a predetermined period. Accordingly, the amplitude value estimated based on each pixel intensity also shows a tendency to gradually increase in the predetermined period as shown in FIG. 3C.

Figure 4:
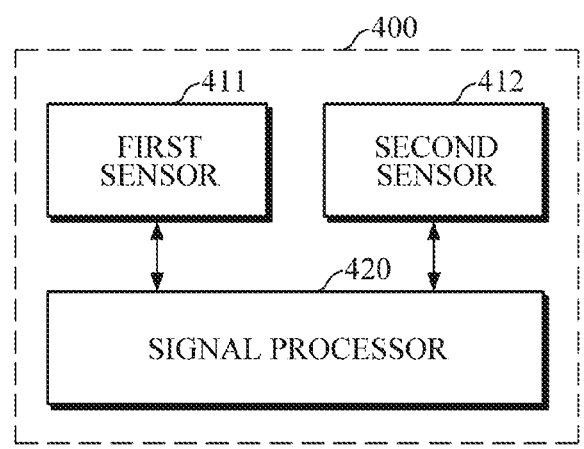
FIG. 4 is a block diagram illustrating an apparatus for measuring a signal according to another exemplary embodiment.
Figure 5A:
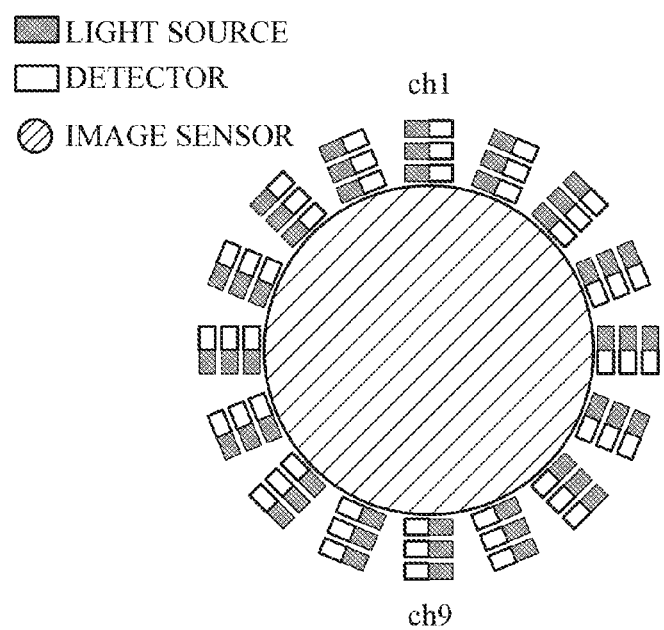
FIGS. 5A and 5B are diagrams for describing a sensor of the apparatus of FIG. 4.
Figure 5B:
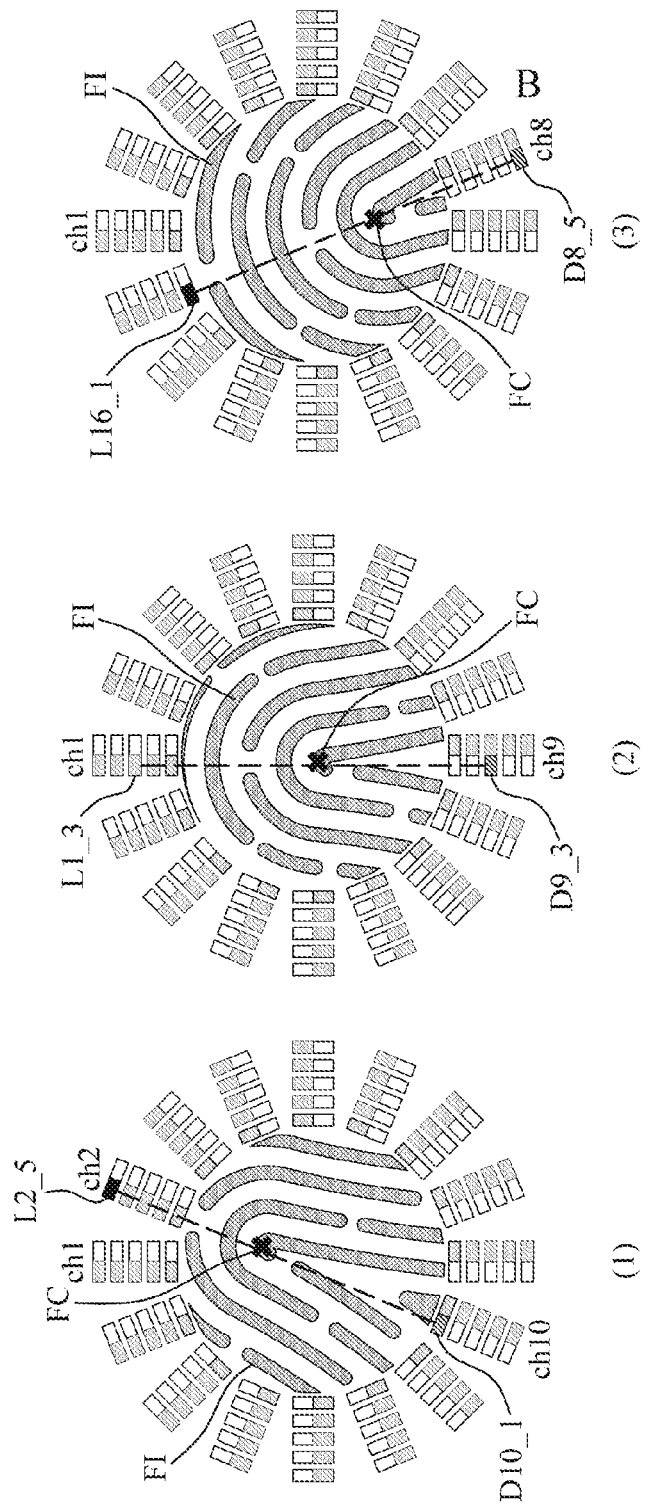

FIG. 4 is a block diagram illustrating an apparatus for measuring a signal according to another exemplary embodiment. FIGS. 5A and 5B are diagrams for describing a sensor of the apparatus of FIG. 4.

Referring to FIG. 4, the apparatus 400 for measuring a signal includes a first sensor 411, a second sensor 412, and a signal processor 420.

The first sensor 411 may generate pixel data representing a contact image of an object according to the contact with the object and transmit the pixel data to the signal processor 420. The first sensor 411 may include a capacitance-type image sensor or fingerprint sensor, but is not limited thereto. The first sensor 411 may include one or more pixels. For example, the first sensor 411 may detects an intensity of each pixel which represents capacitance accumulated in each pixel, and generate information of the intensity of each pixel as pixel data. The intensity of each pixel may increase as the time and/or area of contact between the object and the first sensor 411 increases. In particular, the contact area may be increased as a pressure applied to the first sensor 411 by the user with the object increases.

The second sensor 412 may emit light to the object when the object is in contact with the second sensor 412, and may acquire a target signal by detecting light scattered or reflected from the object. In particular, the second sensor 412 may include a sensor for measuring a pulse wave signal, for example, a PPG signal. However, the second sensor 412 is not limited thereto, and may include a sensor needed according to information to be acquired from the object.

The second sensor 412 may include a plurality of channels, and each channel may include one or more light sources to emit light to the object and one or more detectors to detect light scattered or reflected from the object. In particular, the light source may include an LED or a laser diode, but is not limited thereto. In addition, the detector may include a photodiode or a photo transistor, but is not limited thereto. One or more light sources may emit light rays of different wavelengths.

Referring to FIG. 5A, the first sensor 411 may be formed in a circular shape. As shown in FIG. 5A, the second sensor 412 may have a plurality channels ch1, ..., ch9, which are arranged in an isotropic configuration around the first sensor 412. However, the embodiment is not limited thereto, and the first sensor 411 may be formed in various shapes, such as a rectangle, a triangle, and the like, according to the characteristics of a device in which the apparatus 400 is mounted. For convenience of illustration, FIG. 5A illustrates that the second sensor 412 includes 16 channels and each channel have three light sources and three detectors, but is not particularly limited in the number of components included in the second sensor 412.

The signal processor 420 may be connected to the first sensor 411 to receive the pixel data from the first sensor 411. When the signal processor 420 receives the pixel data from the first sensor 411, the signal processor 420 may acquire a contact image of the object based on the pixel data. In particular, the contact image may be a fingerprint image.

The signal processor 420 may control the driving of the second sensor 412 based on the acquired contact image. For example, the signal processor 420 may extract a feature point from the acquired contact image. In addition, the signal processor 420 may drive the channels of the second sensor 412 based on one or more of a position and a direction of the feature point. For example, the signal processor 420 may drive a first channel located in the direction of the feature point and a second channel located in a direction opposite to the direction of the feature point. Alternatively, the signal processor 420 may determine channels present within a predetermined angle left and right from a line connecting the feature point to the first channel as a first channel group, determine channels present within a predetermined angle left and right from a line connecting the feature point to the second channel as a second channel group, and drive the determined first channel group and second channel group.

In one example, a light source of the first channel or a light source among light sources of the first channel groups which is spaced a predetermined distance apart from the feature point and a detector of the second channel or a detector among detectors of the second channel group which is spaced a predetermined distance apart from the feature point may be continuously driven. In another example, the signal processor 420 may control alternately the driving of the light source of the first channel or the light sources of the first channel group and the detector of the second channel or the detectors of the second channel group and the driving of the detector of the first channel or the detectors of the first channel group and the light source of the second channel or the light sources of the second channel group in a time division manner for a predetermined period of time.

FIG. 5B illustrates an example in which the signal processor 420 drives the channels of the second sensor 412 based on a fingerprint core point FC extracted from a fingerprint image F1 and the orientation of the fingerprint. FIG. 5B illustrates that the second sensor 412 includes 16 channels, each of which includes 5 light sources and 5 detectors. For convenience of description, a light source and a detector nearest to the first sensor 411 are referred to as a first light source and a first detector, and a light source and a detector farthest from the first sensor 411 are referred to as a fifth light source and a fifth detector. In addition, under the assumption that a direction of a channel ch1 from the center of the fingerprint image is a north direction and a direction of a channel ch9 from the center of the fingerprint image is a south direction, the east, west, south, and north directions are defined accordingly.

Referring to an image (1) of FIG. 5B, since the fingerprint is oriented in the slightly north-east direction, the signal processor 420 may drive a first channel ch2 in the north east direction and a second channel ch10 in a direction opposite to the first channel ch2. In particular, the signal processor 420 may drive a fifth light source L2_5 of the first channel ch2 and a first detector D10_1 of the second channel ch10, which are spaced apart from a fingerprint core point FC by a first predetermined distance. Referring to an image (2) of FIG. 5B, since the fingerprint is oriented in the north direction, the signal processor 420 may drive a third light source L1_3 of a first channel ch1 and a third detector D9_3 of a second channel ch9, which are spaced apart from the fingerprint core point FC by a second predetermined distance. Referring to an image (3) of FIG. 5B, since the fingerprint is oriented in the south-west direction, the signal processor 420 may drive a first light source L16_1 of a first channel ch16 and a fifth detector D8_5 of a second channel ch8, which are spaced apart from the fingerprint center FC by a third predetermined distance.

Meanwhile, the signal processor 420 may determine whether a position of the extracted feature point falls outside a normal range on the contact image, and may guide a user to change a contact position of the object when it is determined that the feature point is outside the normal range.

The second sensor 412 may drive a corresponding light sensor and detector to measure a target signal from the object under the control of the signal processor 420, and may transmit the target signal to the signal processor 420.

According to the present embodiment, it is possible to acquire an optimal target signal regardless of the change in contact position and orientation of the object by selectively turning on/off a light source and a detector according to the contact position of the object.

Figure 6:
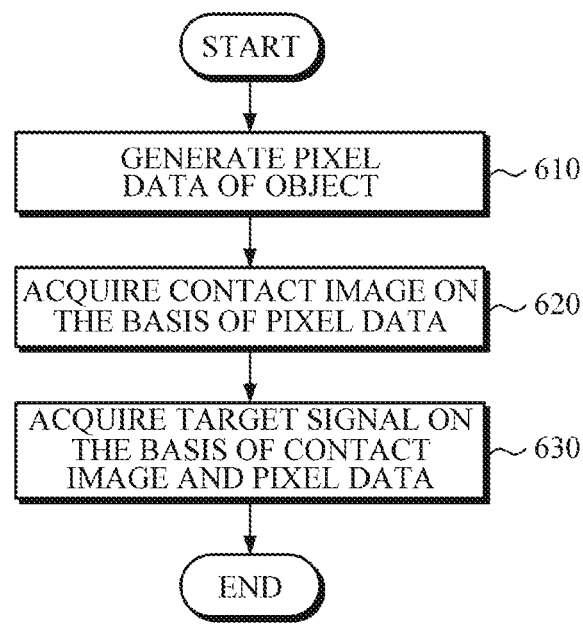
FIG. 6 is a flowchart illustrating a method of measuring a signal according to one exemplary embodiment.
Figure 7A:
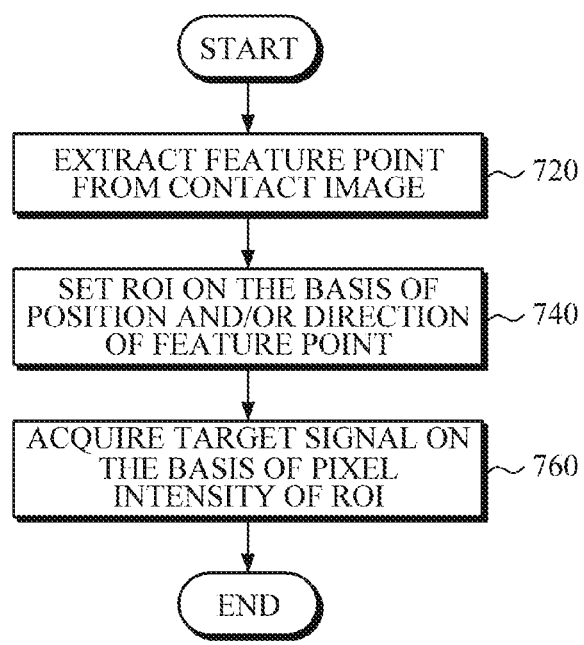
FIGS. 7A and 7B are flowcharts illustrating exemplary embodiments of an operation of acquiring a target signal in FIG. 6.
Figure 7B:
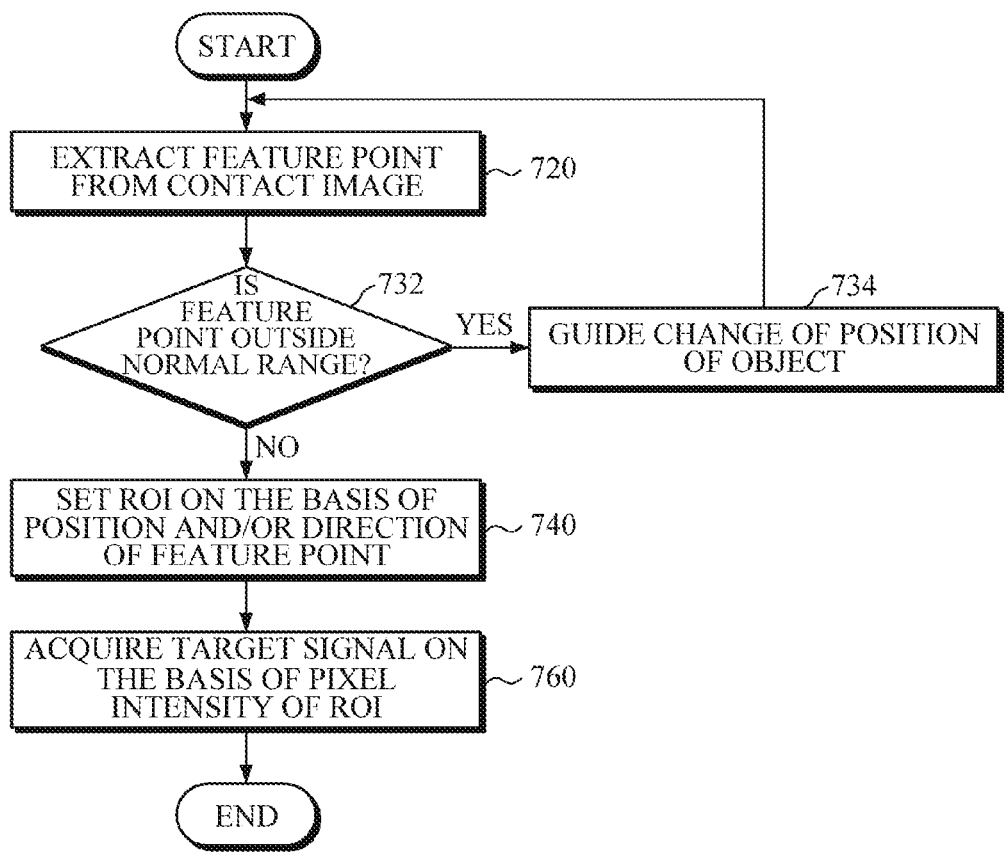

FIG. 6 is a flowchart illustrating a method of measuring a signal according to one exemplary embodiment. FIGS. 7A and 7B are flowcharts illustrating exemplary embodiments of an operation of acquiring a target signal in FIG. 6. FIG. 6 may be one exemplary embodiment of the method performed by the apparatus 100a, 100b, or 100c for measuring a signal according to the exemplary embodiments of FIGS. 1A to 1C. The measuring of a signal is described in detail above, and hence it will be described in detail hereinafter.

First, as an object is in contact with the apparatus for measuring a signal, the apparatus may generate pixel data of the object by detecting light scattered or reflected from the object in operation 610. In particular, the apparatus for measuring a signal may include an optical-based image sensor or fingerprint sensor. The pixel data may be data indicating an intensity of each pixel. In particular, the light input to the object may light emitted by an external light source or light emitted from an internal light source or display panel mounted in the apparatus.

Then, the apparatus may acquire a contact image of the object based on the pixel data in operation 620. At this time, the object may be a finger and the contact image may be a fingerprint image.

Then, the apparatus may acquire a target signal based on the acquired contact image and pixel data in operation 630. In particular, the target signal may be a PPG signal, but is not limited thereto.

Exemplary embodiments of the operation of acquiring the target signal will be described with reference to FIGS. 7A and 7B.

When the contact image is acquired, the apparatus for measuring a signal may extract a feature point based on the contact image in operation 720. In particular, the feature point may be defined in advance according to characteristics of the object. For example, when the object is a finger and the contact image is a fingerprint image, the feature point may be a fingerprint core point.

Meanwhile, according to one exemplary embodiment, as shown in FIG. 7B, whether the feature point falls outside a predetermined normal range may be determined in operation 732. In particular, the normal range may be set according to a center of a detection region of a sensor 110, a center of the contact image, or characteristics of an object of each user. When it is determined in 732 that the feature point is outside the normal range in operation 732, the user may be guided to change a position of the object in operation 734. The apparatus for measuring a signal may guide the user through an output module mounted therein or an output module of an external device, for example, an audio device, a wearable device, a smartphone, a tablet PC, a desktop PC, a healthcare device, and the like, which is connected for communication with the apparatus.

Then, an ROI may be set based on the position and/or direction of the feature point in operation 740. For example, the ROI may be set to various shapes and sizes based on the position of the feature point. That is, a center of the ROI may be located at the position of the feature point. In particular, the ROI may be set based on the direction of the feature point as well, and when the shape of the ROI is, for example, a rectangle or an oval, a long side of the rectangle or a long axis of the oval may be aligned to the direction of the feature point. The center of the ROI is not always necessarily the same as the position of the feature point, and in consideration of, for example, a displacement of the position of the feature point from the center of the contact image, the position of the feature point may have a corresponding displacement from the center of the ROI.

In operations 732 and 740, when the contact image is a fingerprint image, the normal range and the ROI may be determined based on the core point of the fingerprint. The core point may correspond to the center of the north most loop type singularity, or the point of maximum ridge line curve.

Then, a target signal may be acquired based on a pixel intensity within the ROI in operation 760. The target signal may be a PPG signal, and a pulse wave signal for a predetermined period of time may be acquired using a plurality of contact images acquired during a predetermined amount of time. In particular, an amplitude value of the pulse wave signal at a specific point in time may be estimated using a contact image acquired at the specific point in time and the amplitude value at the specific point in time may be calculated by inputting a pixel intensity of the ROI set on the contact image obtained at the specific point in time into a predefined amplitude estimation equation.

Figure 8:
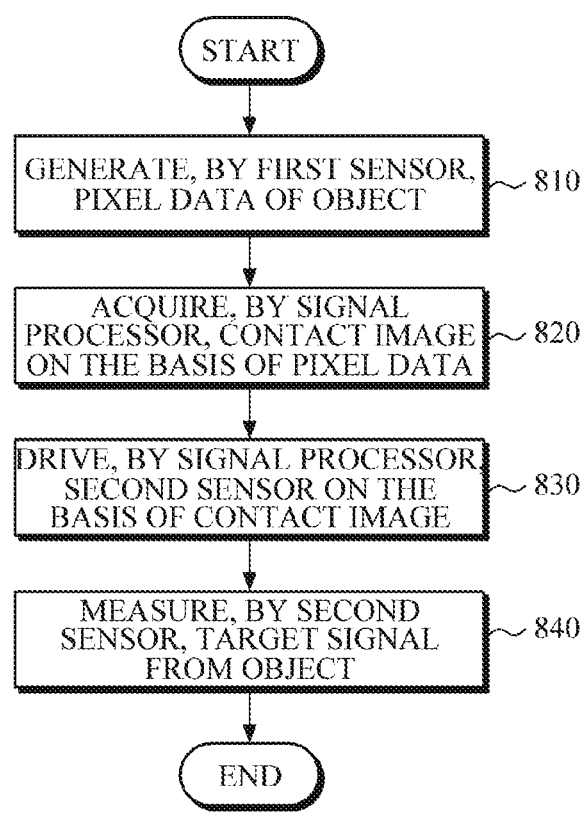
FIG. 8 is a flowchart illustrating a method of measuring a signal according to another exemplary embodiment.

FIG. 8 is a flowchart illustrating a method of measuring a signal according to another exemplary embodiment.

The method illustrated in FIG. 8 may be performed by the apparatus 400 of FIG. 4.

First, a first sensor 411 of the apparatus for measuring a signal may generate pixel data in response to the contact with an object in operation 810. In particular, the first sensor 411 may be a capacitance-based image sensor or fingerprint sensor, but is not limited thereto and may include an optical-based sensor as needed. The fist sensor may include one or more pixels and generate information, such as capacitance accumulated in each pixel in response to the contact with the object, as pixel data.

Then, a signal processor 420 may receive the pixel data and acquire a contact image based on the received pixel data in operation 820. In terms of a technology for acquiring an image of an object using pixel data generated through an image sensor and the like, various well-known methods may be utilized and thus a detailed description thereof will be omitted.

Thereafter, the signal processor 420 may control driving of a second sensor 412 based on the acquired contact image in operation 830. In particular, the second sensor 412 may be a biometric sensor configured to measure a bio-signal, such as a PPG signal, from the object. The second sensor 412 may include a plurality of channels, and each channel may be configured to include one or more light sources and one or more detectors. The signal processor 420 may extract a feature point from the contact image and may drive at least some of the plurality of channels based on a position and/or direction of the extracted feature point. For example, the signal processor 420 may drive one or more channels arranged from the feature point and in a direction of the feature point and one or more channels arranged in a direction opposite to the direction of the feature point.

Then, the second sensor 412 may measure a target signal from the object by driving a corresponding light source and a corresponding detector under the control of the signal processor 420 in operation 840.

Figure 9:
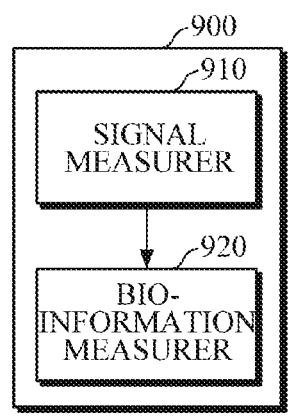
FIGS. 9, 10, and 11 are block diagrams illustrating an apparatus for measuring bio-information according to exemplary embodiments.
Figure 10:
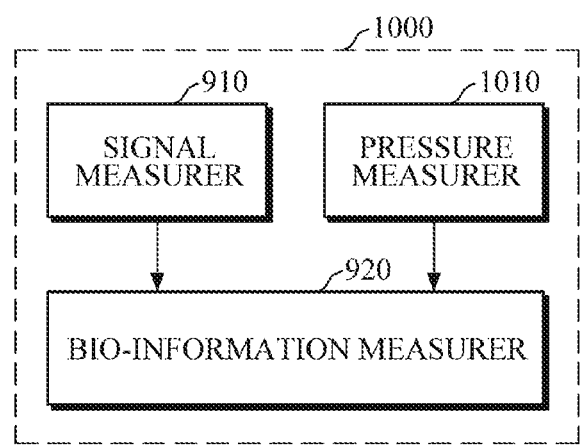
Figure 11:
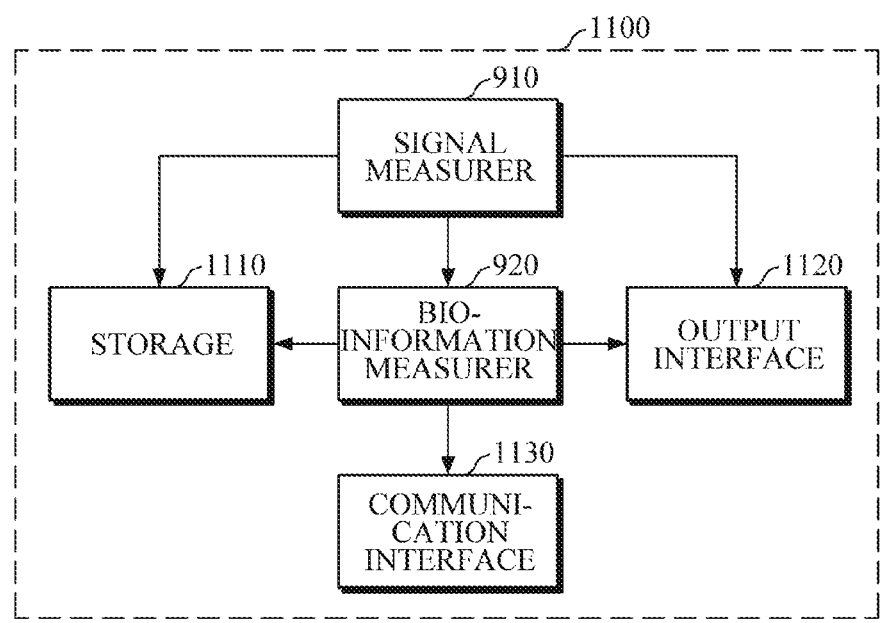

FIGS. 9 to 11 are block diagrams illustrating an apparatus for measuring bio-information according to exemplary embodiments of the present disclosure.

Various exemplary embodiments of the apparatus for measuring bio-information will be described with reference to FIGS. 9 to 11. The exemplary embodiments of the apparatus for measuring bio-information may include the various above-described embodiments of the apparatus for measuring a signal. In addition, the exemplary embodiments of the apparatus for measuring bio-information may be mounted in various information processing devices, such as wearable devices, smart devices, and the like. For example, various information processing devices may include a smart watch worn on a wrist of a user, various types of wearable devices, such as a smart band type, a headphone type, a hairband type, and the like, and mobile devices, such as a smartphone, a tablet PC, and the like. However, the information processing devices are not limited thereto.

Referring to FIG. 9, an apparatus 900 for measuring bio-information may include a signal measurer 910 and a bio-information measurer 920. The signal measurer 910 may correspond to the above-described apparatuses 100a, 100b, 100c, 400 for measuring a signal, or modifications thereof. Therefore, the signal measurer 910 may include the various sensors described above. In addition, various functions related to signal processing performed in the signal measurer 910 and functions of the bio-information measurer 920 are integrated into one processor, or may be separately included in two or more processors.

The signal measurer 910 may include an image sensor configured to generate pixel data representing a contact image of an object when the object is in contact with the signal measurer 910 in response to a request for measuring bio-information. In particular, the image sensor may include various optical-based or capacitance-based sensors, and examples of the image sensor may include a charge coupled device (CCD), a CIS, and a fingerprint sensor.

According to one exemplary embodiment, the image sensor may be configured as a pixel array including a photodetector, such as a photodiode. The signal measurer 910 may include an internal light source configured to emit light to the object. In particular, the internal light source may include an LED or a laser diode, but is not limited thereto. The signal measurer 910 may emit light to the object by driving the internal light source and may detect light scattered or reflected from the object using the image sensor. Meanwhile, the signal measurer 910 may include a display panel and may use light emitted from the display panel as the internal light source. However, the exemplary embodiment is not limited thereto, such that the internal light source may not be mounted according to various conditions, such as a structure of the apparatus 900 for measuring bio-information, and an external light source may be used.

When the pixel data is generated by the image sensor, the signal measurer 910 may acquire a contact image using the pixel data and acquire bio-information based on the acquired contact image. Such operations have been described in detail above with reference to FIGS. 1A to 3C and hence will be omitted thereinafter.

According to another exemplary embodiment, the signal measurer 910 may include a biometric sensor configured to measure a bio-signal, for example, a PPG signal, from the object. In particular, the biometric sensor may be formed by a plurality of channels arranged around the image sensor, and each sensor may include one or more light sources and one or more detectors. In particular, the image sensor may be a capacitance-type sensor that does not have an optical detection function.

When the signal measurer 910 acquires the contact image based on the pixel data obtained from the image sensor, the signal measurer 910 may control driving of the biometric sensor using the acquired contact image. Such an operation has been described in detail above with reference to FIGS. 4, 5A, and 5B, and hence will not be reiterated hereinafter.

Meanwhile, the signal measurer 910 may monitor a contact state of the object based on the contact image and provide a feedback to the user about the contact state. For example, when a feature point (e.g., a fingerprint core point) of the object is not present in the contact image or is outside a predetermined normal range, the signal measurer 910 may guide the user to change a contact position of the object.

The bio-information measurer 920 may acquire bio-information using the bio-signal acquired by the signal measurer 910. In particular, the bio-information may include one or more of blood pressure, vascular age, a degree of arteriosclerosis, aortic pressure waveform, vascular compliance, stress index, and a degree of fatigue, but is not limited thereto.

For example, the bio-information measurer 920 may measure a blood pressure based on an oscillometric scheme using the bio-signal. In particular, the bio-information measurer 920 may estimate a contact pressure based on the pixel data from the image sensor and estimate a blood pressure based on a pulse wave signal and the contact pressure using an oscillometric scheme. As described above, when the contact pressure is increased by increasing a force of a finger pressing the image sensor, a pixel intensity during a predetermined time period accordingly increases. When the pixel data is generated using a contact pressure estimation model indicating a correlation between the contact pressure and the pixel intensity, the bio-information measurer 920 may acquire the contact pressure. At this time, the contact pressure estimation model may be defined in various ways, such as linear/nonlinear function forms, a matching table form, and the like.

Referring to FIG. 10, an apparatus 1000 for measuring bio-information may further include a pressure measurer 1010 in addition to a signal measurer 910 and a bio-information measurer 920. The signal processing function of the signal measurer 910, the function of the bio-information measurer 920, and part of a function of the pressure measurer 1010 may be included in one or more processors.

The pressure measurer 1010 may measure a contact pressure between an object and a biometric sensor when the object is in contact with an image sensor and/or the biometric sensor. In particular, the pressure measurer 1010 may include a force sensor and/or an area sensor and calculate a pressure based on a measured force and/or area.

The contact pressure measurer 1010 may provide guide information to the user about the contact pressure in response to a request for measuring bio-information. In particular, the guide information about the contact pressure may include information about a reference contact pressure which has to be applied by the user during measurement of a bio-signal and/or an actual contact pressure that has been actually applied by the user during the measurement time.

The bio-information measurer 920 may measure bio-information based on the bio-signal acquired by the signal measurer 910 and the contact pressure measured by the pressure measurer 1010.

Referring to FIG. 11, the apparatus 1100 for measuring bio-information may further include a storage 1110, an output interface 1120, and a communication interface 1130 in addition to a signal measurer 910 and a bio-information measurer 920. The signal measurer 910 and the bio-information measurer 920 have been described with reference to FIGS. 9 and 10.

The storage 1110 may store user characteristic information, a variety of reference information necessary to drive a sensor or measure bio-information, a variety of information processed by the signal measurer 910 or the bio-information measurer 920, and the like. Here, the user characteristic information may include user information, such as sex, age, health status, and the like. The reference information necessary to drive a sensor or measure bio-information may include a light emission pattern, a contact position and contact strength of each object, an amplitude estimation equation, a contact pressure estimation model, and the like.

The storage 1110 may include a storage medium such as flash memory, hard disk, multimedia card micro type memory, a card type memory (e.g., SD or XD memory), random access memory (RAM), static random access memory (SRAM), read-only memory (ROM), electrically erasable programmable read-only memory (EEPROM), magnetic memory, magnetic disk, and optical disk, but is not limited thereto.

The output interface 1120 may output a variety of information processed by the signal measurer 910 and the bio-information measurer 920. The output interface 1120 may output user's health status information determined based on a bio-information measurement value. In particular, the output interface 1120 may include a visual output module, such as a display, a voice output module, such as a speaker, and a haptic module for outputting vibration or tactile sensation.

The communication interface 1130 may be connected to various external devices 1200 for wired/wireless communication and receive a variety of reference information from the external devices 1200, or transmit the processing result of the signal measurer 910 or the bio-information measurer 920 to the external devices. The external devices 1200 may include information processing devices, such as a smartphone, a tablet PC, a desktop PC, and the like. The communication interface 1130 may communicate with the external devices using Bluetooth communication, Bluetooth low energy (BLE) communication, near field communication (NFC), wireless local access network (WLAN) communication, ZigBee communication, infrared data association (IrDA) communication, Wi-Fi direct (WFD) communication, ultra-wideband (UWB) communication, Ant+communication, Wi-Fi communication, radio frequency identification (RFID) communication, $3^{rd}$ generation (3G) communication, 4G communication, 5G communication, and the like. However, these are merely examples, and the embodiment is not limited thereto.

Figure 12:
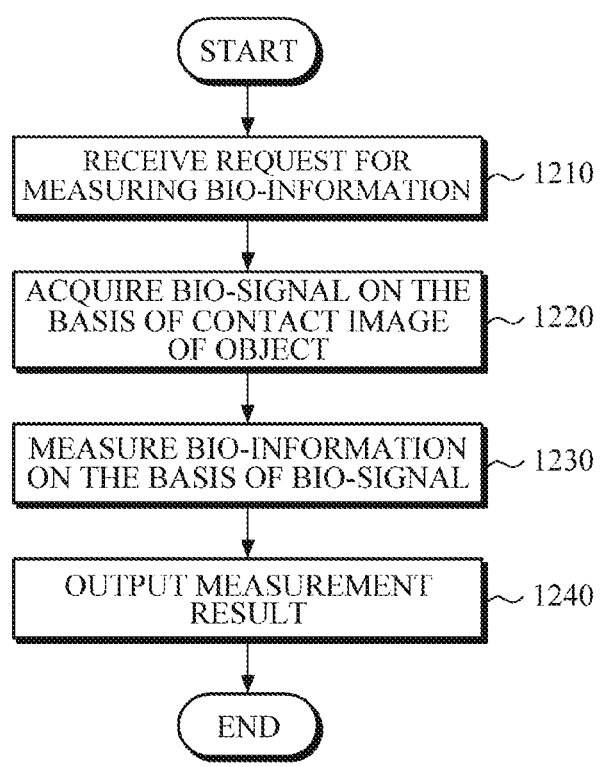
FIG. 12 is a flowchart illustrating a method of measuring bio-information according to exemplary embodiments.

FIG. 12 is a flowchart illustrating a method of measuring bio-information according to embodiments of the present disclosure.

The method shown FIG. 12 corresponds to an exemplary method performed by the apparatuses 900, 1000, and 1100 of FIGS. 9 to 11 to measure bio-information.

First, the apparatus for measuring bio-information may receive a request for measuring bio-information in operation 1210. The request for measuring bio-information may be received from a user or an external device.

Then, a bio-signal may be acquired based on a contact image of an object in operation 1220. The apparatus for measuring bio-information may acquire the contact image based on pixel data that is generated using a capacitance/optical-based image sensor or fingerprint sensor when the object is in contact with the sensor. At this time, the bio-signal may be a PPG signal. For example, the apparatus for measuring bio-information may acquire a pulse wave signal using the pixel data and the contact image. In another example, when a separate biometric sensor for measuring a pulse wave signal is mounted in the apparatus, the apparatus may drive the biometric sensor based on the contact image and measure a pulse wave signal through the biometric sensor.

Then, bio-information may be measured based on the bio-signal in operation 1230. For example, the apparatus for measuring bio-information may measure bio-information, such as blood pressure, based on an oscillometric scheme using the bio-signal. In one example, the apparatus for measuring bio-information may estimate a contact pressure using the pixel data and measure a blood pressure using the estimated contact pressure and the bio-signal. In another example, when a contact pressure sensor is mounted in the apparatus, a blood pressure may be measured using the bio-signal and a contact pressure measured through the contact pressure sensor.

Then, a bio-information measurement result may be output in operation 1240. In particular, the bio-information may be provided to the user using various output modules, such as a display, a speaker module, a haptic module, and the like.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for measuring a signal, the apparatus comprising:
    a sensor configured to generate pixel data representing a fingerprint image of an object by detecting light scattered or reflected from the object; and
    a processor configured to
        acquire the fingerprint image of the object based on the pixel data,
        identify a fingerprint core point in the fingerprint image,
        in response to the fingerprint core point being located within a predetermined distance from a center of the fingerprint image, set a region of interest (ROI) in the fingerprint image to place a center of the ROI at the fingerprint core point and acquire a pulse wave signal based on intensities of pixels in the ROI among the pixel data, and in response to the fingerprint core point not being located within the predetermined distance from the center of the fingerprint image, generate information to guide a user to change of a position of the object.

2. The apparatus of claim 1, wherein the pulse wave signal includes a photoplethysmography (PPG) signal.

3. The apparatus of claim 2, wherein the processor is further configured to estimate an amplitude value of the PPG signal based on the intensities of the pixels in the ROI.

4. The apparatus of claim 3, wherein the processor is further configured to estimate the amplitude value of the PPG signal by calculating at least one of an average, a median value, a lowest value, and a highest value of the intensities of the pixels.

5. The apparatus of claim 1, wherein the processor is further configured to set the ROI based on at least one of a position and an orientation of a feature point comprising the fingerprint core point.

6. The apparatus of claim 1, further comprising one or more light emitting didoes or one or more laser didoes as a light source configured to emit the light to the object.

7. The apparatus of claim 1, further comprising a display panel as a light source configured to emit the light to the object.

8. The apparatus of claim 1, further comprising a light source configured to emit the light to the object in a predetermined light emission pattern under control of the processor, and
wherein the light emission pattern comprises at least one of an emission color and an emission shape including at least one of a straight line shape, a concentric circle shape, a rectangular shape, and a diagonal shape.

9. The apparatus of claim 1, wherein the sensor comprises a pixel array configured to detect the light scattered or reflected from the object and each pixel comprises at least one of a photodiode and a photo transistor.

10. The apparatus of claim 1, wherein the processor is further configured to obtain bio-information based on the pulse wave signal, and
wherein the bio-information comprises at least one of blood pressure, vascular age, a degree of arteriosclerosis, aortic pressure waveform, vascular compliance, stress index, and a degree of fatigue.

11. A method of measuring a signal, the method comprising:
generating pixel data representing a fingerprint image of an object by detecting light scattered or reflected from the object;
acquiring the fingerprint image of the object based on the pixel data;
identifying a fingerprint core point in the fingerprint image;
in response to the fingerprint core point being located within a predetermined distance from a center of the fingerprint image, setting a region of interest (ROI) in the fingerprint image to place a center of the ROI at the fingerprint core point;
acquiring a pulse wave signal based on intensities of pixels in the ROI among the pixel data; and
in response to the fingerprint core point not being located within the predetermined distance from the center of the fingerprint image, generate information to guide a user to change of a position of the object.

12. The method of claim 11, wherein the setting of the ROI comprises setting the ROI based on at least one of a position and an orientation of a feature point comprising the fingerprint core point.

* * * * *